United States Patent [19]

Chen

[11] Patent Number: 5,310,462
[45] Date of Patent: May 10, 1994

[54] QUANTITATION OF SAMPLES UTILIZING CAPILLARY ELECTROPHORESIS

[75] Inventor: Fu-Tai A. Chen, Brea, Calif.

[73] Assignee: Beckman Instruments, Inc., Fullerton, Calif.

[21] Appl. No.: 708,144

[22] Filed: May 31, 1991

[51] Int. Cl.$^5$ .................. G01N 27/26; G01N 27/447
[52] U.S. Cl. ................. 204/180.1; 204/299 R
[58] Field of Search ................. 204/180.1; 264/299 R

[56] References Cited

PUBLICATIONS

Susumu Honda et al "Simultaneous Determination of Iodate and Periodate by Capillary Zone Electrophoresis: Application to Carbohydrate Analysis" Analytical Biochemistry 177 (1989) 62–66.

Honda, "Analysis of the Oligosaccharides in Ovalbumin by High Performance Capillary Electrophoresis", Anal Biochem, 191:228–234 (1990).

Fujiwara, S. & Honda, S. "Determination of Cinnamic Acid & Its Analogues by Electrophoresis in a Fused Silica Capillary Tube"; Anal. Chem. 58:1811–1814 (1986).

Otsuka, K. et al: "Quantitation and Reproducibility in Electrokinetic Chromatography with Micellar Solutions"; J. Chrom. 396 350–354 (1987).

Chen, Fu-Tai A. et al; "Capillary Electrophoresis–a New Clinical Tool"; Clin. Chem. 77/1:14–19 (1991).

Gordan, M. J. et al.; "Protocol for Resolving Protein Mixtures in Capillary Zone Electrophoresis"; Anal. Chem. 63:69–72.

Jorgenson, J. W. and Lukacs; K. D.; "Capillary Zone Electrophoresis"; Science 222:266–272 (1983).

Lauer, H. H. & McManigill, D.; "Capillary Zone Electrophoresis of Proteins in Untreated Fused Silica Tubing"; Anal. Chem. 58:166–170 (1986).

Hoffstetter-Kuhn, S. et al. "Influence of Borate Complexation on the Electrophoretic Behavior of Carbohydrates in Capillary Electrophoresis." Anal. Chem. 63:1541–1547 (1991).

Honda, S. et al. "Simultaneous Determinations of Reducing Monosaccharides by Capillary Zone Electrophoresis as the Borate Complexes of N-Z-Pyridyglycamines". Anal. Biochem. 176:72–77 (1989).

Primary Examiner—John Niebling
Assistant Examiner—John S. Starsiak, Jr.
Attorney, Agent, or Firm—William H. May; P. R. Harder; Janis C. Henry

[57] ABSTRACT

Ionic species and method for the quantitation of sample constituents utilizing capillary zone electrophoresis analysis are disclosed. As disclosed, at least one ionic species having a charge density of betwen about 0.02 and about 0.001 is added to the sample. Benzoic acid is a preferred ionic species. Quantitation of a sample constituent can be derived by normalizing the constituent species with the ionic species.

24 Claims, No Drawings

QUANTITATION OF SAMPLES UTILIZING CAPILLARY ELECTROPHORESIS

RELATED APPLICATIONS

The present application is related to U.S. application Ser. No. 07/708,272, now U.S. Pat. No. 5,120,413, entitled "ANALYSIS OF SAMPLES UTILIZING CAPILLARY ELECTROPHORESIS" filed simultaneously herewith by Fu-Tai A. Chen and James C. Sternberg, and U.S. application Ser. No. 07/708,424, now U.S. Pat. No. 5,139,630, entitled "IDENTIFICATION OF SAMPLE CONSTITUENTS UTILIZING CAPILLARY ELECTROPHORESIS" filed simultaneously herewith by Fu-Tai A. Chen.

FIELD OF THE INVENTION

The present invention is related to analysis of samples in general, analysis by capillary zone electrophoresis in particular, and specifically to quantitation of sample species using capillary zone electrophoresis.

BACKGROUND OF THE INVENTION

The articles set forth in the Background of the Invention are each incorporated herein by reference.

Mammalian proteins present in clinical samples (e.g. whole blood, serum, plasma, cerebrospinal fluid, and urine) are useful as indicators of a disease state or a bodily condition. The amount and type of these proteins in the sample can provide a wealth of information to the clinician.

For example, the protein components of serum include albumin, alpha-1 lipoprotein, alpha-2 macroglobulin, beta-1 lipoprotein and immunoglobulins (including gammaglobulins). Albumin, the major protein of serum, is usually present in a concentration of between 4.0 and 5.0 g/dL. Decreased concentration of albumin can be indicative of renal disease; increased concentration of albumin is characteristic of dehydration. Elevated levels of alpha-1 lipoprotein can be indicative of chronic alcoholism or hyperestrogenism due to, e.g., pregnancy. Elevated levels of beta-1 lipoprotein can be indicative of increased cholesterol levels.

Mammalian proteins are charged proteins containing both cationic and anionic moieties. They thus lend themselves to analysis by capillary zone electrophoresis ("CZE"). CZE is a technique which permits rapid and efficient separations of charged substances. In general terms, CZE involves introduction of a sample into a capillary tube and the application of an electric field to the tube. The electric field pulls the sample through the tube and separates it into its constituent parts. I.e., each of the sample constituents has its own electrophoretic mobility; those having greater mobility travel through the capillary faster than those with slower mobility. As a result, the constituents of the sample are resolved into discrete zones in the capillary tube during the migration of the sample through the tube. An on-line detector can be used to continuously monitor the separation and provide data as to the various constituents based upon the discrete zones. The detector measures the absorbance of light by each constituent at a specified wavelength; different constituents absorb light differently, and, because of this, the constituents can be differentiated from each other.

CZE can be generally separated into two categories based upon the contents of the capillary columns. In "gel" CZE, the capillary tube is filled with a suitable gel, e.g. polyacrylamide gel. Separation of the constituents in the sample is predicated in part by the size and charge of the constituents travelling through the gel matrix. In "open-tube" CZE, the capillary tube is filled with an electrically conductive buffer solution. Upon application of an electric field to the capillary, the negatively charged capillary wall will attract a layer of positive ions from the buffer. As these ions flow towards the cathode, under the influence of the electrical potential, the bulk solution must flow in this direction to maintain electroneutrality. This electroendosmatic flow provides a fixed velocity component which drives both neutral species and ionic species, regardless of charge, towards the cathode. The buffer in open CZE is as stable against conduction and diffusion as the gels utilized in gel CZE. Accordingly, separations can be obtained in open CZE quite similar to those obtained in gel-based electrophoresis.

Typically, the pH of the buffers utilized in open CZE are chosen with reference to the isoelectric points (pI) of the constituents in the sample. For example, the pI of serum albumin is 4.6; therefore, at pH 4.6, negatively charged and positively charged moieties of serum albumin are equal and the overall charge is neutral. However, as the pH is raised above the isoelectric point, the negatively charged moieties predominate and the net charge is negative. Thus, by selection of the proper pH, all of the species of the sample will be negatively charged. For serum samples, at pH greater than about 8.00, the majority of all serum-protein species will be negatively charged. Thus, manipulation of the isoelectric points of sample species can be used to ensure a proper charge distribution vis-a-vis the flow of such species through a charged capillary.

Typically, the results of CZE analysis are provided via an electropherogram, which depicts the discrete zones of the sample constituents as peaks of various height and width. Additionally, the results can be presented in terms of numerical data based upon the integrated area under each constituent peak.

From analysis of clinical samples, it is possible to determine a disease state or bodily condition by comparing the peaks obtained in an electropherogram of the sample with those obtained in an electropherogram of a known control. Thus, if a sample constituent peak from a clinical sample electropherogram is broader or more narrow or higher or not as high relative to the same sample constituent peak from the control electropherogram, it may be indicative of a disease state or a bodily condition.

A problem with CZE analysis of protein-containing samples, peptide-containing samples, and samples containing native and/or synthetic DNA and RNA, is that it is very difficult to accurately quantify the individual sample constituents. I.e, while it has been possible to visually compare relative peaks to determine if a potential disease condition exists, it has heretofore been a problem to accurately and consistently determine the precise quantitative amounts of the individual constituents of the sample.

Another problem encountered with capillary zone electrophoresis of such samples is that the constituents may appear on the electropherogram at different migration times with different samples. Stated again, a protein and/or peptide common to two different samples may show up at a different place on each of the electropherograms for such samples. This is due, in part, to the fact that the amount of time taken by each earlier sample constituent as it passes through the capillary will affect the migration time of latter sample constituents.

Previous attempts at quantitation of sample constituents have been reported. Cinnamic acid has been attempted as an internal standard for the determination of ferulic acid concentration in dog plasma after oral administration of γ-oryzanol. Fujiwara, S. and Honda, S. "Determination of Cinnamic Acid and its Analogues by Electrophoresis in a Fused Silica Capillary Tube." *Anal. Chem.* 58:1811-1814 (1986). Phenol has been attempted as an internal standard for the determination of chlorinated phenol concentrations. Otsuka, K. et al. "Quantitation and Reproducibility in Chromatography with Micellar Solutions." *J. of Chrom.* 396:350-354 (1987). Additionally, coinjection of a known amount of a species to be analyzed is well documented.

Internal standards, i.e. standards that are detected within the constituent detection region, can lead to at least two problems. First, there is the potential for co-migration. The internal standard may migrate at or near a region where a sample constituent migrates leading to erroneous analysis of that constituent. This is because the sample constituent may appear to have a peak of greater height or width based upon its mixing with and the effect of the co-migrating standard. Second, because the amount of sample analyzed can affect its flow rate, the location of the internal standard peak on the electropherogram can vary depending on the amount of sample analyzed. If the peak location of the internal reference is artificially altered, quantitation of constituents based on such alterations would be inaccurate, incomprehensible or erroneous.

Accordingly, a need exists for an efficient and reliable method for rapidly quantifying protein-and/or peptide containing sample constituents using a capillary zone electrophoresis protocol.

SUMMARY OF THE INVENTION

The present invention satisfies this need by adding at least one ionic species to the sample to be analyzed and using the known concentration of that ionic species as the basis for determining the concentration of the constituents of the sample. By "ionic species" is meant a species having a charge density of between about 0.02 and about 0.001. "Charge density" is defined as the number of negative charges of a species divided by the molecular weight of that species. In the most preferred embodiment of the invention, the ionic species has a single negative charge, and a molecular weight of between about 50 and about 750, more preferably between about 75 and 250 and most preferably between about 100 and about 160.

The ionic species is selected relative to the charge density of the constituents of the sample transiting the capillary column. The intent is that the electropherogram peak of the ionic species be well defined and not overlap with the peaks of any of the sample constituents. In the most preferrred embodiment of the present invention, the charge density of the ionic species is greater than that that of each of the major constituents of the sample. In this embodiment, the electropherogram peak of the ionic species appears after the electropherogram peak of the last major sample constituent.

The known concentration of the ionic species can be used to determine the concentration of each particular sample constituent. The ionic species is added to a sample to form a mixture. This mixture is then subjected to capillary zone electrophoresis, and the ionic species and constituent species from the sample are detected by an on-line detector. Each particular constituent species can be accurately quantified based upon normalizing the individual constituent species relative to the ionic species added to the sample, the electropherogram integrated area peak of the ionic species and the integrated area peaks for each of the sample constituents.

These and other advantages will be set forth in detail in the following detailed disclosure.

DETAILED DESCRIPTION OF PREFERRED EMBODIMENTS

For simplicity of presentation this portion of the disclosure is directed to quantitation of clinical samples. It is understood, however, that the present invention is equally applicable to quantitation of peptide-containing samples, protein-containing samples other than clinical samples and samples containing native and/or synthetic DNA or RNA.

The problems of the prior art are avoided by the present inventive method of adding at least one ionic species to the sample to be analyzed.

In the most preferred embodiment of the present invention, the ionic species has a charge density greater than that of the last major constituent of the sample being analyzed. It will thus pass the on-line detector and appear as a peak on the resultant electropherogram after most, if not all, of the sample constituents. Each sample constituent is then quantified based on information known about the ionic species (to be described in detail below), and the size of the electropherogram peak of the ionic species relative to the size of the electropherogram peaks of each sample constituent.

A. The Ionic Species

The principal criteria for the ionic species is the location of its electropherogram peak relative to that of the sample constituents. It is essential that the electropherogram peak for the ionic species be well defined and not overlap with the peaks of any of the constituent species of interest. Accordingly, it is possible for the ionic species peak to appear within the area where species peaks appear. Most preferably, the ionic species is detected after the last major component of the analyzed sample. Thus, the ionic species should have a "flexible" flow rate, i.e. the ionic species should be able to, in effect, adapt to the sample by "lagging behind" the last sample constituent zone, irrespective of the deviation in sample volume or conditions. This criteria for the ionic species is determined by the "charge density" of the standard.

The charge density is a measure of the "speed" at which either a constituent in the sample being analyzed, or the ionic species, will travel through the capillary. A constituent having a higher charge density will migrate more slowly through the capillary compared to a constituent having a lower (relative) charge density. If the ionic species is to pass the on-line detector after the last sample constituent, then the charge density of the ionic species must be greater than the charge density of the last sample constituent.

The "charge density" of a species is defined as the number of negative charges of a species divided by the molecular weight of that species. The charge density of the ionic species is preferably between about 0.02 and about 0.001, more preferably between about 0.01 and about 0.004, and most preferably between about 0.01 and about 0.006. In the most preferred embodiment of the present invention, the ionic species has a single negative charge such that its molecular weight is preferably between about 50 and about 750, more preferably between about 75 and about 250, and most preferably between about 100 and about 160. However, the ionic species can have several negative charges; as the number of negative charges are increased, the molecular weight of that species must also increase such that the charge density continues to be within the desired range of from about 0.02 to about 0.001.

The negative charge of the species is dereived from a "negative charge moiety" of that species. By "negative charge moiety" is meant either at least one carboxylic acid moiety, or at least one sulfonic acid moiety, or at least one phosphoric acid moiety, or at least one phenylate moiety, or at least one thiophenylate moiety. Upon ionization or when pH is greater than the pI, these moieties will be negatively charged. As is appreciated by those in the art, phosphoric acid has from between 1 and 3 negative charges. Under acidic conditions (i.e. about pH 4), phosphoric acid has a single negative charge; under neutral conditions (i.e. pH about 7), phosphoric acid has two negative charges; and under basic conditions (i.e. pH of about 9), phosphoric acid has three negative charges.

As previously noted, the pH of the buffers used in open CZE are chosen with reference to the isoelectric points of the constituents of the sample. The objective is to determine the pH at which all of the constituents will be negatively charged. For serum, this is a pH greater than about 8.00. Thus, the ionic species is preferably stable in aqueous solutions having a pH of at least about 8.00. It is also desirable for the ionic species to have absorbance characteristics similar to those of peptide bonds so that the ionic species will be detected by the on-line detector along with the sample constituents. This is because the constituents of clinical sample are comprised of protein species, and protein species include peptide bonds. Thus, the ionic species preferably has an absorbance of less than about 300 nm, more preferably less than about 250 nm, and most preferably between about 220 nm and about 200 nm.

The particular structural conformation of the ionic species is not, in and of itself, important. Thus, cyclic-, straight chain-, or branched-ionic species having the required negative charge moiety can be used, provided that the charge density thereof is between about 0.02 to about 0.001.

Examples of ionic species include formic acid (1 negative charge; molecular weight of 48; charge density of 0.02), acetic acid (1;60;.017), benzophosphoric acid (2;158;0.013), propionic acid (1;74; 0.014), isopropionic acid (1;74;0.014), butyric acid (1;88;0.011), isobutyric acid (1;88;0.011), benzoic acid (1;122;0.008), benzo-sulfonic acid (1;148;0.007), orthochloro benzoic acid, meta-chloro benzoic acid, and parachloro benzoic acid, (1;157;0.006), naphthyl sulfonic acid (1;208;0.005), benzo-naphthalinic acid (1;224;0.004), chloro-benzo naphthalinic acid (1;258:0.004), chloronaphthyl sulfonic acid (1;242;0.004), tetra-iodo benzo naphthyl sulfonic acid (1;716;0.001), and di-iodo anthracenyl sulfonic acid (1;776;0.001). Most preferably, benzoic acid is utilized as the ionic species.

For efficiency and speed of analysis, it is desirable to utilize an ionic species which is detected within a relatively brief period after the detection of the last sample constituent. "Relatively brief" is defined as less than about two minutes; longer times may, however, also be used.

B. Constituent Charge Density

As indicated, the ionic species is selected such that its relative charge density will produce a unique and well defined electropherogram peak. In the most preferred embodiment of the invention, the charge density of the ionic species is greater than that of the major constituents of the sample. As such, the ionic species is detected after the last major constituent of the sample being analyzed. Accordingly, the charge densities of the sample constituents must be determined, or for the most preferred embodiment of the invention, the charge density of the last major constituent must be determined.

Clinical samples include peptide and protein species. Peptides and proteins are made from an assortment of 20 amino acids. Each amino acid has a side chain. One method of catagorizing amino acids is based upon whether these side chains are acidic, basic, uncharged-polar or non-polar. Lysine, arginine and histidine have basic side chains; asparagine, glutamine, serine, threonine and tyrosine have uncharged-polar side chains; glycine, alanine, valine, leucine, isoleucine, proline, phenylalanine, methionine, tryptophan, and cysteine have non-polar side chains; and aspartic acid and glutamic acid have acidic side chains. Of the 20 amino acids, only aspartic acid and glutamic acid, because of their acidic side chains, will maintain a net negative charge upon ionization.

Accordingly, while charge density is defined as the number of negative charges of a species divided by the molecular weight of that species, the charge density of peptides, proteins and native and/or synthetic DNA or RNA can also be determined by dividing the number of aspartic acid and glutamic acid amino acids contained in these species by the molecular weight of that species.

C. Determination of Ionic Species Concentration

The concentration of the ionic species in the sample is based upon a combination of the desired integrated area for the ionic species; the dilution of the sample; the protein concentration from a normal control; and a value derived from the absorbance values at fixed wavelengths of fixed volume amounts of the ionic species and the sample.

The integrated area of the electropherogram ionic species peak should be less than about 50% of the total integrated area for the sample constituent peaks and the ionic species peak. This is because the integrated area of the ionic species should not be so great as to diminish the integrated areas of the sample constituents; an integrated area for the ionic species peak of greater than about 50% would cause such a diminishing affect on the other electropherogram peaks. Preferably, the integrated area should be between about 5% and about 40% of the total integrated area, and most preferably about 30% of the total integrated area.

CZE analysis usually involves dilution of the sample being analyzed. For example, serum, plasma, and whole blood are diluted prior to introduction to the capillary in order to assist these samples in flowing through the capillary; urine and cerebro-spinal fluid can be diluted, but dilution is not a requirement. Dilution is typically from about 1 part sample to about 20 parts diluent (1:20=0.05), to about 1:100(0.01). Most preferably, where dilution is desirable, the dilution ratio is 1:50(0.02). Diluents which can be used and which are applicable to the present invention are well known and varied and will not be discussed herein. A representative diluent is ICS ™ Diluent (Beckman Instruments, Inc.) The diluent should preferably have a neutral pH (i.e. about 7).

The protein concentration from a control is selected to have a concentration of protein equal to that normally present in a typical normal human sample. For example, the protein concentration from a serum sample of a healthy individual is about 60 mg/ml. Similar concentration values for urine and cerebrospinal fluid ("CSF") are about 10 μg/ml and between about 150 and about 400 μg/ml, respectively. Thus, if a patient serum protein concentration is above or below these normal values, a clinical problem may exist. For consistency of concentration terms, the protein concentration present in human serum is about 60,000 μg/ml.

A further factor needed in the determination of the amount of ionic species added to the sample is based upon the absorbance of defined amounts of the ionic species and the sample at the fixed wavelengths detected by the on-line detector. When a defined amount of the ionic species and the sample are irradiated with light at a fixed wavelength, a numerically defined absorbance value for each can be determined. These two values are used to provide a ratio of absorbance for the ionic species alone and the sample alone. These values are obtained separately so as to determine the absorbance characteristics of each without interference from the other.

In order to determine the concentration of the ionic species in the sample ("I.S."), the above factors are mathematically manipulated by multiplying the normal protein concentration of the particular sample being analyzed by the dilution factor (for CSF, a mid-point value of 275 μg/ml can be used for the protein concentration); this value is then multiplied by the desired integrated area of the ionic species; finally, the total is multiplied by: the quotient derived from the absorbance value of a defined amount of the ionic species measured at a fixed wavelength divided by the absorbance value of the same defined amount of the sample measured at about the same fixed wavelength.

The foregoing may be symbolically represented as follows:

$$I.S. = (S*D*P.W.)*X/Y \quad (1)$$

As used throughout the disclosure, the symbol "*" is meant to indicate a mathematical multiplication symbol. In this equation, S is the desired integrated area percentage of the ionic species peak as defined above; D is the dilution factor of the sample as defined above (for samples that are not diluted such as urine or cerebro spinal fluid, this value can be 1.0); P.W. is the normal protein concentration; X is the absorbance of (most preferably) 100 μg/ml of the ionic species at a fixed wavelength; and Y is the absorbance of 100 μg/ml of sample at a fixed wavelength. Thus, both X and Y are absorbance values typically expressed in nanometers. With respect to the absorbance values and the amount of ionic species and sample measured, this particular amount is not of import per se; what is important is that the amounts utilized for both the sample and the ionic species be about the same.

D. Determination of Constituent Concentration

To determine the concentration of the constituents of the sample, the integrated area of each sample constituent and ionic species peak is determined, and the relative percentage of each peak to the total integrated areas of all such peaks is derived. Each peak percentage is then normalized relative to the ionic species. As used herein, the term "normalized" means that certain criteria regarding the ionic species itself and the ionic species as measured by CZE analysis are manipulated such that the concentration of each constituent species can be obtained from the ionic species.

Accordingly, to determine the concentration of a particular species ("P.S."), the integrated area value of that species, is divided by the integrated area value of the ionic species. This value is multiplied by: the inverse of the dilution factor; the absorbance value of a defined amount of the sample measured at a fixed wavelength, which is divided by the absorbance value of about the same defined amount of the ionic species measured at about the same fixed wavelength (i.e. Y/X, the inverse of the manipulation of these factors as described in Section C, "Determination of Ionic Species Concentration"); and the concentration of the ionic species in the sample.

The foregoing may be symbolically represented as follows:

$$P.S. = \frac{SC\%}{S\%} * \left( \frac{1}{D} * \frac{Y}{X} * [I.S.] \right) \quad (2)$$

where SC% represents the integrated area percentage of at least one constituent species; S% represents the integrated area percentage of the ionic species; D represents the dilution factor; Y/X represents the inverse of the absorbance manipulation factor as previously defined in Section C, "Determination of Ionic Species Concentration;" and [I.S.] is the concentration of the ionic species in the anaylzed sample.

EXAMPLES

The following examples directed to preferred embodiments of the invention disclosed herein are not intended, nor should they be construed, as limiting the disclosure, or the claims to follow.

A. Materials and Methods

I. Capillary Electrophoresis Procedures

Capillary electrophoresis of clinical samples and controls were performed on a Beckman Instruments, Inc. high performance capillary electrophoresis system (Beckman Instruments, Inc., Fullerton, Calif., USA, Model No. 357575). Data analysis was performed on System Gold ™ software (Beckman Instruments, Inc.). The aforementioned capillary electrophoresis system contains built-in 214, 254, 280 and 415 nM narrow-band filters for on-line detection. Electrophoresis was performed in a fused silica tube, 75 μm i.d. and 25 cm long (Polymicro Technologies, Inc., Phoenix, Ariz. USA, Product No. TSP075375). The detection window was located approximately 6.5 cm from the column outlet.

Clinical samples and controls were placed on the inlet tray of the above-described capillary electrophoresis system. Clinical samples and controls were automatically injected into the capillary tube by the electrokinetic method for 3 to 10 seconds at 1 kV. Analysis was performed in less than 10 minutes using a column voltage gradient of 200 volts/cm. The capillary tube was washed and reconditioned between each run (18 seconds in NaOH, 12 seconds 0.1% Triton-X 100 TM in distilled H₂O).

II. Electrophoresis Buffer

Electrophoresis buffer was made in accordance with the disclosure of the co-pending application referenced above, by dissolving 9.95 g of boric acid (MW 61.83) and 4.86 g sodium hydroxide (MW 40.00) in 1 L distilled H₂O. Final concentration of boric acid was 80 mM/L and final pH was adjusted to 10.25±0.1 by dropwise addition of 1N NaOH.

III. Reagents

All chemicals were at least of ACS grade. Benzoic acid (Aldrich Chemical, Milwaukee, Wis., USA, Part No. 24,238-1) was added to ICS TM Diluent (Beckman Instruments, Inc., Part No. 449690) such that the final benzoic acid concentration was 0.10 mg/ml; an example of how the benzoic acid concentration was derived will be set forth in Example II. Protein standard utilized was I.D. - Zone TM Normal Protein Electrophoresis Control (Beckman Instruments, Inc., Part No. 667600). A 1:50 protein control:diluted marker ratio was utilized.

Patient serum samples were obtained from Brea Community Hospital, Brea, Calif. A 1:50 serum sample:diluted internal marker ratio was utilized.

IV. Comparative Instrumentation

For CZE analysis of the protein control comparisons, a Synchron CX ®4 clinical analyzer (Beckman Instruments, Inc.) was utilized to determine total protein and albumin concentrations. Manufacturer instructions were followed for the protein control analysis.

B. EXAMPLES

EXAMPLE I

Protein Charge Density Estimation

The charge density for the protein species can be readily and effectively calculated for purposes of determining the charge density of the ionic species either by a determination of the number of aspartic acid and glutamic acid amino acids in the protein, as outlined above, by conventional sequencing techniques such as, for example, the [Sanger-Coulson or Maxam-Gilbert] Edman degradation methods, or by protein sequencing instruments such as, for example, the PI 2020 TM and PI 2090E TM protein sequencers (Porton Instruments, Inc., Tarzana, Calif.)

Following the outlined procedure, for example, the last major component of human serum to be detected by CZE analysis is albumin (pre-albumin is the absolute last component of serum). Serum albumin (human) has a molecular weight ("MW") of about 86,000. Each amino acid has an approximate molecular weight of about 100. Therefore, for human serum albumin ("HSA"):

$$\frac{86,000 \text{ MW}}{100 \text{ MW}/a.a.} = 860 \text{ amino acids}$$

Thus, there are approximately 860 amino acids in HSA. Theoretically, because there are twenty amino acids in HSA, approximately five percent of the HSA amino acids should be aspartic acid, and approximately five percent should be glutamic acid; i.e. 10% of the approximate 860 HSA amino acids should have a net negative charge upon ionization. However, for calculation purposes, it is considered prudent to double this theoretical approximation to 20% in order to estimate a theoretical maximum negative charge. Doubling the contribution of negatively charged moieties to the constituent will not impose a deleterious impact upon the amount of ionic species utilized. Therefore, for purposes of calculation, in order to determine the approximate charge density of HSA:

$$20\% \times 860 \, a.a. = 172 \text{ carboxylic acid moieties}$$
$$\frac{172}{86,000 \text{ MW}} = \frac{1}{500} = .002$$
$$= \text{the approximate charge density of } HSA$$

Therefore, for the ionic species to travel slower than the last sample constituent, in this case, HSA, the charge density of the ionic species must be greater than 0.002.

The foregoing methodology can be readily utilized for any amino-acid containing constituent. I.e., the molecular weight of the constituent(s) can be used to provide an accurate estimate of the charge density thereof such that the electropherogram peak of the ionic species can be positioned as a unique and defined peak relative to the peak(s) of the constituent(s). By dividing the molecular weight of the amino-acid containing constituent by 100 (the approximate molecular weight of an amino acid); multiplying this value by 20% (the theoretical maximum number of aspartic acid and glutamic acid amino acids in a protein species); and dividing this value by the molecular weight of the constituent, a charge density value for that constituent is provided which can be used for purposes of determining the charge density of the ionic species.

Benzoic acid, having one carboxylic moiety and a molecular weight of 122, has a charge density of 1/122 (0.008) which is greater than the charge density of HSA (0.002).

EXAMPLE II

Standard Amount Determination

As previously outlined, the concentration of the ionic species in the sample can be determined as follows:

$$(S*D*P.W.)*X/Y$$

Definitions for each factor in the equation are fully detailed above. A most preferred ionic species is benzoic acid. As noted, the most preferred value for S is 30%. For the analysis of serum, a most preferred dilution factor is 1:50 (0.02). The protein concentration of human serum is about 60 mg/ml. The absorbance values for the defined amounts of benzoic acid and the sample (100 μl), measured at a fixed wavelength of 214 nm, were 0.4471(X) and 1.66(Y), respectively; therefore, the value is 0.2693 (0.4471/1.66). Accordingly, the concentration (and hence amount) of benzoic acid in the sample is derived as follows:

$$(0.30*0.02*60)*0.2693 = 0.097 \text{ mg/ml}$$

For the examples to follow, this value was rounded upwards such that the concentration of benzoic acid in the standard was 0.10 mg/ml.

EXAMPLE III

Determination of Constituent Concentration Factor

As noted, the integrated area of each constituent species is normalized relative to certain ascertainable information for the ionic species. While the information regarding integrated areas must be determined from the CZE analysis of the sample, the remaining factors can be determined based upon the data set forth in Example II. Equation 2, without the integrated area portion thereof, provides the following:

$$\frac{1}{D} \cdot \frac{Y}{X} \cdot [I.S.]$$

The solution to this portion of the equation is referred to as the "ionic species normalizing value".

Using the values as defined and derived in Example II, for the clinical samples used in the following examples (serum), the ionic species normalizing value can be derived as follows:

$$\frac{1}{.02} \cdot 3.713 \cdot .10 \text{ mg/ml} = 18.57 \text{ mg/ml}$$

Example IV
Protein Control
CZE

The aforementioned protein control was analyzed using the aforementioned Beckman high performance capillary zone electrophoresis system, with detection at 214 nM and an applied potential of 5 kV. Analytical results were obtained in less than 10 minutes. The integrated area values (as automatically derived by the system Gold ™ software) are set forth in Table 1, infra; sample constituent concentration values, as derived, are set forth in Table 2, infra.

EXAMPLE V

Protein Control SYNCHRON CX ® 4

The protein control of Example IV was analyzed on the aforementioned Beckman Synchron CX ®4 clinical analyzer for total protein and albumin concentrations. Concentration values are set forth in Table 2, infra.

EXAMPLE VI

Patient Serum CZE

Nine patient serum samples (1–9) were analyzed in accordance with the procedure outlined in Example IV. Integrated area values are set forth in Table 1, infra; sample constituent concentration values as derived in accordance with the present invention are set forth in Table 2, infra.

EXAMPLE VII

Patient Serum SYNCHRON CX ® 4

The patient-serum samples of Example VI were analyzed for Total Protein and Albumin concentrations in accordance with the procedure outlined in Example V. Concentration values as obtained from the analytical instrument are set forth in Table 2, infra.

TABLE 1

| | Integrated Area Values (%) | | | | | |
|---|---|---|---|---|---|---|
| | A | B | C | D | E | F |
| Control | 11.78 | 10.12 | 5.97 | 5.64 | 43.25 | 22.92 |

TABLE 1-continued

| | Integrated Area Values (%) | | | | | |
|---|---|---|---|---|---|---|
| | A | B | C | D | E | F |
| 1 | 40.25 | 5.39 | 4.59 | 3.03 | 26.58 | 20.17 |
| 2 | 15.37 | 7.38 | 6.00 | 3.64 | 45.08 | 22.58 |
| 3 | 14.54 | 5.04 | 7.80 | 2.58 | 47.79 | 21.88 |
| 4 | 16.56 | 8.51 | 4.27 | 3.20 | 45.95 | 21.59 |
| 5 | 13.79 | 8.85 | 6.29 | 3.44 | 45.95 | 26.26 |
| 6 | 6.58 | 11.53 | 5.80 | 4.50 | 44.84 | 20.65 |
| 7 | 25.44 | 6.37 | 5.50 | 5.14 | 36.33 | 21.72 |
| 8 | 3.24 | 7.63 | 13.96 | 7.22 | 46.07 | 21.91 |
| 9 | 15.00 | 9.65 | 4.66 | 4.13 | 32.39 | 24.17 |

A = Gammaglobulin
B = Beta 1 Lipoprotein
C = Alpha 1 Lipoprotein
D = Alpha 2 Macroglobulin
E = Albumin
F = Benzoic Acid The values for SC% and S% are obtained from Table 1 as described above and the ionic species normalizing value is as previously calculated (18.57 mg/ml). Accordingly, sample constituent concentrations are readily calculated, and these are presented in Table 2.

TABLE 2

| | Constituent Concentrations (mg/ml) | | | | | | | |
|---|---|---|---|---|---|---|---|---|
| | A | B | C | D | E | F | G | H |
| Control | 9.7 | 8.3 | 4.9 | 4.7 | 35.7 | 37.0 | 63.3 | 62.0 |
| 1 | 37.1 | 5.0 | 4.2 | 2.8 | 24.5 | 26.0 | 73.5 | 78.0 |
| 2 | 12.6 | 6.0 | 4.9 | 3.0 | 32.1 | 37.1 | 63.7 | 63.0 |
| 3 | 12.3 | 4.3 | 6.6 | 2.2 | 40.5 | 46.0 | 65.9 | 73.0 |
| 4 | 14.3 | 7.3 | 3.7 | 2.8 | 39.6 | 38.0 | 67.7 | 66.0 |
| 5 | 12.0 | 7.7 | 5.5 | 3.0 | 40.1 | 44.0 | 68.4 | 74.0 |
| 6 | 4.6 | 8.0 | 4.0 | 3.1 | 31.0 | 34.0 | 50.8 | 54.0 |
| 7 | 22.8 | 6.2 | 4.9 | 4.6 | 32.5 | 36.0 | 71.0 | 78.0 |
| 8 | 2.7 | 6.5 | 11.8 | 6.1 | 39.0 | 40.0 | 66.2 | 64.0 |
| 9 | 11.5 | 7.4 | 3.6 | 3.2 | 32.6 | 38.0 | 58.2 | 64.0 |

A = Gammaglobulin
B = Beta 1 Lipoprotein
C = Alpha 1 Lipoprotein
D = Alpha 2 Macroglobulin
E = Albumin (CZE)
F = Albumin (SYNCHRON CX ® 4)
G = Total Protein (CZE) (sum of A through E)
H = Total Protein (SYNCHRON CX ® 4)

Regression analysis for the comparisons between the CZE analysis for albumin and total protein and Synchron CX ®4 ("CX4") analysis for albumin and total protein are as follows:

| Albumin |
|---|
| $Y_{CZE} = (1.0463 \cdot X_{CX4}) - 2.141$ |
| $R = .9603$ |
| Total Protein |
| $Y_{CZE} = (1.0864 \cdot X_{CX4}) - 4.138$ |
| $R = .8467$ |

As the above results demonstrate, the concentration of clinical sample constituents can be accurately and rapidly determined by CZE by use of an ionic species as disclosed herein. Furthermore, because each of the sample constituents is defined, a more definitive analysis is provided. I.e., for Patient #2, review of the total protein concentration alone indicates that, relative to the protein control, the total protein is acceptable. However, a review of the gammaglobulin concentration indicates that the value is elevated relative to the control, possibly indicative of a potential disease state or bodily condition. Accordingly, the foregoing data demonstrates the advantages and benefits which are derived from CZE analysis of clinical samples utilizing at least one ionic species for the determination of sample constituent concentration.

While the foregoing standard and methodology have been described in considerable detail and in terms of preferred embodiments, these are not to be construed as limitations on the disclosure or the claims that follow. The invention is not to be limited to the particular Beckman high performance capillary electrophoresis system described. Modifications and changes that are within the purview of those skilled in the art are intended to fall within the scope of the following claims.

What is claimed is:

1. A method of quantifying a peptide-containing constituent species in a sample by capillary zone electrophoresis comprising the following steps:
   a) adding at least one ionic species to the sample to form a mixture, the ionic species having a charge density greater than substantially all of the peptide-containing constituent species in the sample,
   b) subjecting the mixture to capillary zone electrophoresis,
   c) detecting the ionic species and the peptide-containing constituent species in said mixture, and
   d) normalizing at least one peptide-containing constituent species relative to the detected ionic species, where the normalized value of step (d) is the quantified amount of said peptide-containing constituent species in the sample.

2. The method of claim 1 wherein the charge density of the ionic species is between about 0.02 and about 0.001.

3. The method of claim 1 wherein the charge density of the ionic species is between about 0.01 and about 0.004.

4. The method of claim 1 wherein the charge density of the ionic species is between about 0.01 and about 0.006.

5. The method of claim 1 wherein the ionic species comprises at least one negative charge and has a molecular weight of at least about 50.

6. The method of claim 1 wherein said ionic species is soluble in an aqueous medium at pH greater than about 8.00.

7. The method of claim 1 wherein said ionic species has an absorbance at less then about 300 nm.

8. The method of claim 1 wherein the concentration of said ionic species added to the sample is determined by multiplying a dilution factor of the sample by the protein concentration for a normal control to obtain a first value; multiplying a desired integrated area percentage of the ionic species by the first value to obtain a second value; and multiplying the second value by a third value, the third value derived by dividing an absorbance value of a fixed amount of the ionic species measured at a fixed wavelength by an absorbance value of about the same fixed amount of the sample measured at about the same fixed wavelength.

9. The method of claim 8 wherein the desired integrated area percentage is a value less than about 0.50.

10. The method of claim 8 wherein the desired integrated area percentage is a value between about 0.05 and about 0.40.

11. The method of claim 8 wherein the desired integrated area percentage is about 0.30.

12. The method of claim 8 wherein the dilution factor is a value between about 0.05 and about 0.01.

13. The method of claim 8 wherein the dilution factor is about 0.02.

14. The method of claim 8 wherein the protein concentration is between about 10 $\mu$g/ml and about 60,000 $\mu$g/ml.

15. The method of claim 8 wherein the protein concentration is about 60 mg/ml.

16. The method of claim 1 wherein said ionic species is selected from the group consisting of formic acid, acetic acid, benzo-phosphoric acid, propionic acid, isopropionic acid, butyric acid, isobutyric acid, benzoic acid, benzo-sulfonic acid, ortho-chloro benzoic acid, meta-chloro benzoic acid, para-chloro benzoic acid, naphthyl sulfonic acid, benzo naphthalinic acid, chlorobenzo naphthalinic acid, chloro-naphthyl sulfonic acid, tetra-iodo benzo naphthyl sulfonic acid, and di-iodo anthracenyl sulfonic acid.

17. The method of claim 1 wherein said ionic species is benzoic acid.

18. The method of claim 17 wherein the concentration of said benzoic acid in said sample is about 0.10 mg/ml.

19. The method of claim 1 wherein said normalizing of at least one peptide-containing constituent species is determined by dividing an integrated area value of at least one peptide-containing constituent species by the total integrated area amounts from the analysis to obtain a first value; dividing the first value by a second value to obtain a third value, the second value derived by dividing the integrated area value of the ionic species by the total integrated area amounts from the analysis; multiplying the third value by a fourth value, the fourth value derived by dividing the dilution factor of the sample by the numeral 1.0 to obtain a fifth value; multiplying the fifth value by a sixth value, the sixth value derived by dividing an absorbance value of a fixed amount of the sample measured at a fixed wavelength by an absorbance value of about the same fixed amount of the ionic species measured at about the same fixed wavelength; and multiplying the sixth value by the concentration of the ionic species in the sample.

20. A method of quantifying peptide-containing constituent species in a clinical sample by capillary zone electrophoresis comprising the following steps:
   a) adding at least one ionic species having a charge density of between about 0.02 and about 0.001 to the sample to form a clinical mixture, the charge density of the ionic species being greater than substantially all of the constituent species in the clinical sample;
   b) separating said clinical mixture into its constituent parts by capillary zone electrophoresis;
   c) detecting the ionic species and the peptide-containing constituent species in said mixture; and
   d) normalizing at least one peptide-containing constituent species by dividing the integrated area value of said peptide-containing species by the total integrated area values from all of the peptide-containing constituent species to obtain a first value; dividing the first value by a second value to obtain a third value, the second value being obtained by dividing the integrated area value of the ionic species by the total integrated area amounts from the constituent species; multiplying the third value by a fourth value, the fourth value being the dilution factor of the sample to obtain a fifth value; multiplying the fifth value by a sixth value, the sixth value being obtained by dividing the absorbance value of a fixed amount of the sample measured at a fixed wavelength by the absorbance value of about the same fixed amount of the ionic species measured at about the same fixed wavelength; and multiplying the sixth value by the concentration of the ionic species in the sample.

21. The method of claim 20 wherein said ionic species is selected from the group consisting of formic acid, acetic acid, benzo-phosphoric acid, propionic acid, iso-propionic acid, butyric acid, isobutyric acid, benzoic acid, benzo-sulfonic acid, ortho-chloro benzoic acid, meta-chloro benzoic acid, para-chloro benzoic acid, naphthyl sulfonic acid, benzo naphthalinic acid, chloro-benzo naphthalinic acid, chloro-naphthyl sulfonic acid, tetra-iodo benzo naphthyl sulfonic acid, and di-iodo anthracenyl sulfonic acid.

22. The method of claim 20 wherein said ionic species is benzoic acid.

23. A method of quantifying peptide-containing constituent species in a sample by capillary electrophoresis comprising the following steps:
    a) adding at least one ionic species to the sample to form a mixture, the ionic species having a charge density less than substantially all of the peptide-containing constituent species in the sample,
    b) subjecting the mixture to capillary zone electrophoresis,
    c) detecting the ionic species and the peptide-containing constituent species in said mixture, and
    d) normalizing at least one peptide-containing constituent species relative to the detected ionic species,
where the normalized value of step (d) is the quantified amount of said peptide-containing constituent species in the sample.

24. A method of quantifying peptide-containing constituent species in a clinical sample by capillary zone electrophoresis comprising the following steps:
    a) adding at least one ionic species having a charge density of between about 0.02 and about 0.001 to the clinical sample to form a clinical mixture, the charge density of the ionic species being less than substantially all of the peptide-containing constituent species in the clinical sample;
    b) separating said clinical mixture into its constituent parts by capillary zone electrophoresis;
    c) detecting the ionic species and the constituent peptide-containing species in said mixture; and
    d) normalizing at least one peptide-containing constituent species by dividing the integrated area value of said peptide-containing species by the total integrated area values from all of the constituent peptide-containing species to obtain a first value; dividing the first value by a second value to obtain a third value, the second value being obtained by dividing the integrated area value of the ionic species by the total integrated area amounts from the constituent peptide-containing species; multiplying the third value by a fourth value, the fourth value being the dilution factor of the clinical sample to obtain a fifth value; multiplying the fifth value by a sixth value, the sixth value being obtained by dividing the absorbance value of a fixed amount of the clinical sample measured at a fixed wavelength by the absorbance value of about the same fixed amount of the ionic species measured at about the same fixed wavelength; and multiplying the sixth value by the concentration of the ionic species in the clinical sample.

* * * * *